United States Patent [19]

Nagabhushan

[11] 4,226,808

[45] Oct. 7, 1980

[54] 1-ARYL-2-DIHALOGENODEUTERIOALK-ANOYLAMIDO-1,3-PROPANEDIOL ANTIBACTERIAL AGENTS

[75] Inventor: Tattanahalli L. Nagabhushan, Parsippany, N.J.

[73] Assignee: Schering Corporation, Kenilworth, N.J.

[21] Appl. No.: 67,267

[22] Filed: Aug. 17, 1979

[51] Int. Cl.$^2$ ............... C07C 103/127; C07C 69/63; C11C 3/00; A61K 31/165
[52] U.S. Cl. ............... 260/562 B; 260/556 AR; 260/465 F; 260/410.5; 560/155; 560/193; 424/312; 424/313; 424/320; 424/321
[58] Field of Search ........ 260/562 B, 556 AR, 465 F, 260/410.5; 560/155, 193

[56] References Cited

PUBLICATIONS

Kutter et al., "Journal of Medicinal Chemistry", vol. 14, No. 10, (1971), pp. 931–934.

*Primary Examiner*—Joseph E. Evans
*Attorney, Agent, or Firm*—Mary S. King

[57] ABSTRACT

Described are D-(threo)-1-p-substituted phenyl-2-dihalogeno-α-deuterioalkanoylamido-1,3-propanediols and their use as antibacterial agents.

10 Claims, No Drawings

1-ARYL-2-DIHALOGENODEUTERIOALK-ANOYLAMIDO-1,3-PROPANEDIOL ANTIBACTERIAL AGENTS

FIELD OF INVENTION

This invention relates to novel compositions-of-matter, to methods for their preparation, and to methods for their use as antibacterial agents.

More specifically, this invention relates to novel 1-aryl-2-dihalogenodeuterioalkanoylamido-1,3-propanediol antibacterial agents, to methods for their manufacture, to pharmaceutical compositions comprising said 1-aryl-2-dihalogenodeuterioalkanoylamido-1,3-propanediols, and to methods for their use in treating antibacterial infections.

In particular, this invention relates to D-(threo)-1-p-substituted-phenyl-2-dihalogenodeuterioalkanoylamido-1,3-propanediol antibacterial agents, including the deuterio derivatives of chloramphenicol, of the difluoroacetyl analog of chloramphenicol, of thiamphenicol, fluorthiamphenicol, tevenel and fluortevenel (i.e., the difluoroacetyl analog of tevenel), and to the 3-hydrocarboncarboxylate (preferably 3-carboxyhydrocarboncarboxylate) esters and 3-(aminohydrocarboncarboxylate) esters thereof and their pharmaceutically acceptable salts, as well as methods for their preparation and their use as antibacterial agents.

PRIOR ART

Known in the art are broad spectrum antibiotics which may be classified as D-(threo)-1-p-substituted phenyl-2-dihalogenoacetylamido-1,3-propanediols, including chloramphenicol (D-threo)-1-p-nitrophenyl-2-dichloroacetamido-1,3-propanediol), thiamphenicol (D-(threo)-1-p-methylsulfonylphenyl-2-dichloroacetamido-1,3-propanediol), fluorthiamphenicol (D-(threo)-1-p-methylsulfonylphenyl-2-difluoroacetamido-1,3-propanediol) and tevenel (D-(threo)-1-p-aminosulfonylphenyl-2-dichloroacetamido-1,3-propanediol).

Also known in the art is that replacement of the benzylic hydrogen in chloramphenicol (i.e., the hydrogen on the carbon to which the p-nitrophenyl group is bonded) with a deuterium atom to produce α-deuteriochloramphenicol causes reduction in antibacterial activity, the activity of α-deuteriochloramphenicol against *Escherichia coli* having been found to be only about 80% the chloramphenicol activity (E. Kutter and H. Machleidt, J. Med. Chem., Vol. 14, No. 10, 931–934 (1971)).

By my invention, I have found that surprisingly, replacement of the hydrogen in the dichloroacetyl side chain in chloramphenicol with a deuterium atom to produce D-(threo)-1-p-nitrophenyl-2-dichlorodeuterioacetamido-1,3-propanediol, causes an increase in antibacterial activity, e.g., the activity of the foregoing 2-dichlorodeuterioacetamido derivative against bacteria which are susceptible to chloramphenicol is about 50% greater than that of chloramphenicol.

GENERAL DESCRIPTION OF THE INVENTION COMPOSITION-OF-MATTER ASPECT

In its composition-of-matter aspect, the invention sought to be patented resides in the concept of D-(threo)-1-p-substituted-2-dihalogenodeuterioacetyl (or 1',2'-dihalogeno-1'-deuteriopropionyl)-1,3-propanediols useful as antibacterial agents.

Included among the antibacterially active compositions-of-matter of this invention are D-(threo)-1-p-substitutedphenyl-2-dihalogenodeuterioalkanoylamido-1,3-propanediols of the following formula I:

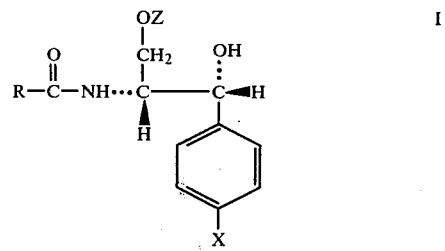

wherein R is a member selected from the group consisting of dihalogenodeuteriomethyl and 1,2-dihalogeno-1-deuterioethyl;

X is a member selected from the group consisting of $NO_2$, $SO_2R_1$, $SOR_1$, $SR_1$, $SONH_2$, $SO_2NH_2$, $SONHR_1$, $SO_2NHR_1$, $COR_1$, halogen, hydrogen, phenyl and phenyl substituted by halogen, $NO_2$ or $SO_2CH_3$, wherein $R_1$ is methyl, ethyl, n-propyl or isopropyl;

and Z is hydrogen or an acyl radical of a hydrocarboncarboxylic acid (preferably a hydrocarbondicarboxylic acid) having up to 16 carbon atoms or an acyl radical of an amino hydrocarboncarboxylic acid having up to 12 carbon atoms; and the pharmaceutically acceptable salts of said acyl radicals.

Included among the halogenated alkyl groups contemplated for the moiety R is this invention are the difluoro-, dichloro- and dibromo-deuteriomethyl groups as well as 1,2-difluoro-, 1,2-dichloro-, 1,2-dibromo-1-deuterioethyl groups. Also included are mixed dihalogenoalkyl groups, e.g., groups such as fluorochloro-, fluorobromo-, and chlorobromodeuteriomethyl and 1-chloro-2-fluoro-, 1-chloro-2-bromo-, 1-fluoro-2-chloro, 1-fluoro-2-bromo, 1-bromo-2-fluoro- and 1-bromo-2-chloro-1-deuterioethyl. Thus, the dihalogenodeuterioalkanoyl groups contemplated by this invention

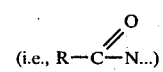

include dihalogenodeuterioacetamido derivatives as well as α,β-dihalogeno-α-deuteriopropionamido derivatives. Of the foregoing, preferred are compounds of formula I wherein

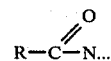

is dichlorodeuterioacetamido, difluorodeuterioacetamido, fluorochlorodeuterioacetamido.

Of the 1-p-substituted phenyl derivatives of formula I contemplated by this invention, preferred are the 1-p-nitrophenyl (i.e., X is $NO_2$), the 1-p-methylsulfonylphenyl (i.e., X is $SO_2CH_3$), and the 1-p-aminosulfonylphenyl (i.e., X is $SO_2NH_2$).

The compounds of formula I have two assymetric centers at carbons 1 and 2 of the propanol structure and, therefore, have four possible stereoisomers. The preferred stereoisomer of my invention is the one in which the absolute configuration is D and the relative configuration is threo. Thus, the compounds defined by formula I have the D-(threo)- configuration, which is the same isomeric form present in the prior art antibiotics chloramphenicol and the difluoroacetyl analog thereof, thiamphenicol, fluorthiamphenicol, and tevenel.

In addition to the foregoing, when R is a mixed dihalogenodeuteriomethyl, an assymetric center exists within the acylamido group

at the carbon to which the halogen is bonded. It is to be understood that both stereoisomeric forms within the acylamido group as well as racemates thereof are included within the concept of my invention.

Of particular interest are compounds of formula I having a 1-p-nitrophenyl or a 1-p-methylsulfonylphenyl group and a 2-dichlorodeuterioacetamido or a 2-difluorodeuterioacetamido or a 2-(chlorofluorodeuterioacetamido) group which are deuterio derivatives of chloramphenicol and the difluoroacetyl analog thereof, thiamphenicol and fluorthiamphenicol, and of their corresponding 2-(chlorofluoroacetamido) derivatives thereof. These are D-(threo)-1-p-nitrophenyl-2-dichlorodeuterioacetamido-1,3-propanediol (R=Cl$_2$CD; X=NO$_2$); D-(threo)-1-p-nitrophenyl-2-difluorodeuterioacetamido-1,3-propanediol (R=F$_2$CD; X=NO$_2$); D-(threo)-1-p-methylsulfonylphenyl-2-dichlorodeuterioacetamido-1,3-propanediol (R=Cl$_2$CD; X=SO$_2$CH$_3$); D-(threo)-1-p-methylsulfonylphenyl-2-difluorodeuterioacetamido-1,3-propanediol (R=F$_2$CD; X=SO$_2$CH$_3$) and the 2-(chlorofluorodeuterioacetamido) analogs of the foregoing, e.g., D-(threo)-1-p-nitrophenyl-2-(R,S-chlorofluorodeuterioacetamido)-1,3-propanediol (R=ClFCD; X=NO$_2$). The foregoing compounds advantageously have enhanced antibacterial activity against organisms susceptible to their precursor non-deuterioated antibiotics. Thus, these compounds are broad spectrum antibacterial agents having greater activity than chloramphenicol or thiamphenicol, and are useful in the treatment of gram positive, gram negative and rickettsial infections.

Other valuable broad spectrum antibacterial agents of formula I include:

D-(threo)-1-p-aminosulfonylphenyl-2-dichlorodeuterioacetamido-1,3-propanediol (R is Cl$_2$CD—; X is NH$_2$SO$_2$), a derivative of tevenel);

D-(threo)-1-p-aminosulfonylphenyl-2-difluorodeuterioacetamido-1,3-propanediol (R is F$_2$CD—; X is NH$_2$SO$_2$), a derivative of fluortevenel;

D-(threo)-1-p-methylsulfinylphenyl-2-dichlorodeuterioacetamido-3-fluoro-1-propanol (R=Cl$_2$CD; X=SOCH$_3$); and D-(threo)-1-p-methylsulfinylphenyl-2-difluorodeuterioacetamido-3-fluoro-1-propanol (R=F$_2$CD; X=SOCH$_3$).

Also included among the antibacterially active compounds of this invention are the ester derivatives, e.g., 3-hydrocarboncarboxylates of formula I wherein Z is an acyl radical of a hydrocarboncarboxylic acid having up to 16 carbon atoms which may be saturated, unsaturated, straight chain or branched chain, aliphatic, cyclic, cyclic-aliphatic, aromatic, aryl-aliphatic, or alkylaromatic and may be substituted by hydroxy, alkoxy containing from 1 to 5 carbon atoms, carboxyl or halogen. The 3-hydrocarboncarboxylates of the D-(threo)-1-(p-substitutedphenyl)-2-dihalogenodeuterioalkanoylamido-1,3-propanediols of my invention are thus derived from hydrocarboncarboxylic acids such as alkanoic acids exemplified by formic, acetic, propionic, trimethylacetic, butyric, isobutyric, valeric, isovaleric, caproic, tert.-butylacetic, enanthic, caprylic, capric, cyclopentylpropionic, undecylic, lauric, palmitic, and adamantanecarboxylic acids; substituted alkanoic acids such as phenoxyacetic and pantothenic acids; aromatic and substituted aromatic acids including benzoic, toluic, p-methoxybenzoic, and 3',5'-dimethylbenzoic acids, arylalkanoic acids such as phenylacetic, phenylpropionic, and β-benzoylaminoisobutyric acids, unsaturated acids such as acrylic, cinnamic, and sorbic acids; and, preferably, dibasic acids such as succinic, tartaric, and phthalic acids.

Other antibacterially active ester derivatives of formula I are those wherein Z is an acyl radical of a neutral amino acid containing up to 12 carbon atoms and which may be saturated, unsaturated, straight chain, branched chain or cyclic, which may contain aromatic groups and which may be substituted by hydroxyl groups. Amino acid ester derivatives of formula I are thus compounds wherein Z is derived from a neutral amino acid such as tryptophan, threonine, serine, hydroxyproline, proline, tyrosine, phenylalanine, isoleucine, leucine, valine, alanine, and, preferably, glycine.

Preferred ester derivatives of my invention include those derived from dibasic hydrocarboncarboxylates, e.g., the 3-succinate and 3-phthalate esters, which provide water soluble, pharmaceutically acceptable cationic salts, e.g., the sodium or potassium salts as well as salts with an amine, e.g., trimethylamine and arginine. Also preferred are ester derivatives of amino acids, e.g., glycinate ester, which provide water soluble, pharmaceutically acceptable acid addition salts with mineral or organic acids, e.g., the hydrochloric, or sulfuric acid, or the succinic acid addition salts.

The term "pharmaceutically acceptable salts" of this invention thus includes salts wherein the acidic hydrogen in the dibasic hydrocarboncarboxylate esters of this invention is replaced with a cation (e.g., sodium D-(threo)-1-p-nitrophenyl-2-dichlorodeuterioacetamido-1,3-propanediol hemisuccinate) as well as salts wherein the acidic hydrogen forms an acid addition salt with an amine (e.g., D-(threo)-1-p-nitrophenyl-2-dichlorodeuterioacetamido-1,3-propanediol hemisuccinate N-trimethylamine salt and the N-arginine salt). Also included in the term "pharmaceutically acceptable salts" are the acid addition salts formed between mineral or organic acids and the amine in the amino acid esters of this invention (e.g., D-(threo)-1-p-methylsulfonylphenyl-2-dichlorodeuterioacetamido-1,3-propanediol glycinate hydrochloride).

Among the pharmaceutically acceptable cationic salts of the dibasic hydrocarboxylate esters contemplated for this invention are salts of alkali and alkaline earth metals (e.g., sodium, potassium, calcium, aluminum) and salts with an amine such as trialkylamines, procaine, dibenzylamine, N-benzyl-beta-phenethylamine, N,N'-dibenzylethylenediamine, N,N'-bis-dehydroabietylethylenediamine, N-(lower)alkylpiperidines (e.g., N-ethylpiperidine), and N-methyl glucamine.

The pharmaceutically acceptable cationic salts (e.g., the sodium salt, trimethylamine or arginine salt) are prepared according to knownl procedures such as by combining equimolar quantities of the corresponding base (e.g., sodium hydroxide or trimethylamine or arginine) to the dibasic hydrocarboncarboxylate ester derivative (e.g., D-(threo)-1-p-nitrophenyl-2-dichlorodeuterioacetamido-1,3-propanediol 3-hemisuccinate) in the aqueous solution and lyophilizing the resultant solution of the dibasic hydrocarboxylate salt (e.g., sodium D-(threo)-1-p-nitrophenyl-2-dichlorodeuterioacetamido-1,3-propanediol 3-hemisuccinate or D-(threo)-1-p-nitrophenyl-2-dichlorodeuterioacetamido-1,3-propanediol hemisuccinate trimethylamine salt or D-(threo)-1-p-nitrophenyl-2-dichlorodeuterioacetamido-1,3-propanediol hemisuccinate arginine salt.

The pharmaceutically acceptable acid addition salts of the 3-propyl amino acid ester derivatives of this invention (e.g., D-(threo)-1-p-methylsulfonylphenyl-2-dichlorodeuterioacetamido-1,3-propanediol 3-glycinate hydrochloride) are made according to known procedures such as by neutralizing the free base (e.g., D-(threo)-1-p-methylsulfonylphenyl-2-dichlorodeuterioacetamido-1,3-propanediol 3-glycinate) with an appropriate acid (e.g., hydrochloric acid) to about pH 5. Suitable acids for this purpose include acids such as hydrochloric, sulfuric, phosphoric, nitric, hydrobromic, acetic, propionic, maleic, ascorbic, citric and the like.

The physical embodiments of the pharmaceutically acceptable salts of this invention are characterized by being white or off-white solids which are soluble in water, sparingly soluble in most polar solvents, and insoluble in most non-polar organic solvents.

The D-(threo)-1-p-substituted phenyl-2-dihalogenodeuterioalkanoylamido-1,3-propanediol derivatives of this invention such as defined by formula I including the non-toxic, pharmaceutically acceptable salts thereof, in general, exhibit broad spectrum antibacterial activity and possess improved antibacterial activities compared to the parent antibiotics, i.e., to the corresponding non-deuterated compounds. Thus, for example, the compounds of this invention, as defined by formula I, particularly the D-(threo)-1-p-nitrophenyl- and D-(threo)-1-p-methylsulfonylphenyl-2-dichlorodeuterioacetamido-1,3-propanediols as well as the corresponding 2-difluorodeuterioacetamido and 2-chlorofluorodeuterioacetamido analogs are more active against organisms sensitive to chloramphenicol and thiamphenicol than their non-deuterated precursors.

Particularly useful compounds of my invention are those wherein R is diahalogeno-deuteriomethyl or $\alpha,\beta$-dihalogeno-1-deuterioethyl, X is aminosulfonyl, nitro or methylsulfonyl. Of these, a paticularly valuable group are the D-(threo)-1-p-nitrophenyl- and the D-(threo)-1-p-methylsulfonylphenyl-1,3-propanediol derivatives of formula I, particularly the 2-dichlorodeuterioacetamido-, 2-difluorodeuterioacetamido, and 2-chlorofluorodeuterioacetamido derivatives thereof, which are broad spectrum antibiotics, being active against gram positive bacteria (e.g., *Staphylococcus aureus*) and gram negative bacteria (e.g., *Escherichia coli, Hemophilus influenzae,* Klebsiella, Salmonella, Shigella, Proteus, Enterobacter, and Serratia) as determined by standard dilution tests. Particularly useful antibacterials of this invention are D-(threo)-1-p-nitrophenyl-2-dichlorodeuterioacetamido-1,3-propanediol; D-(threo)-1-p-nitrophenyl-2-difluorodeuterioacetamido-1,3-propanediol; D-(threo)-1-p-methylsulfonylphenyl-2-dichlorodeuterioacetamido-1,3-propanediol; and D-(threo)-1-p-methylsulfonylphenyl-2-difluorodeuterioacetamido-1,3-propanediol, as well as the corresponding 2-(R,S-chlorofluorodeuterioacetamido) derivatives thereof.

PROCESS ASPECT OF THE INVENTION

Compounds of formula I wherein R is a dihalogenodeuteriomethyl or an $\alpha,\beta$-dihalogeno-1-deuterioethyl are prepared from the corresponding non-deuterated compound of formula I wherein R is dihalogenoalkyl, utilizing conventional deuterium exchange reactions, e.g., utilizing methyl alcohol-D (i.e., $CH_3OD$).

The D-(threo)-1-p-substitutedphenyl-2-dihalogenomethyl (or $\alpha,\beta$-dihalogenoethyl)-1,3-propanediol precursors are either known compounds or are prepared from known compounds via procedures well known in the art.

Thus, for example, the non-deuterated analogs of the mixed dihalogenoalkanoylamido derivatives of formula I (e.g., compounds of formula I wherein

is fluorochloroacetylamido) are prepared from the corresponding D-(threo)-1-p-substituted-phenyl-2-amino-1,3-propanediols by converting the 2-amino function to a 2-dihalogenoalkanoylamido function by reaction thereof with a lower alkanoic acid derivative such as chlorofluoroacetic acid anhydride or chloride or with a lower alkyl ester of said halogeno alkanoic acids (e.g., methyl chlorofluoroacetate) in a lower alkanol (e.g., an alkanol having up to 4 carbon atoms) said alkanoic acid derivatives being known compounds or conveniently prepared by known techniques.

Alternatively, in the above procedure, by treating the amine with a dihalogenodeuterioalkanoic acid ester, halide, or anhydride (prepared via conventional deuterium exchange reactions) there is obtained directly D-(threo)-1-p-substitutedphenyl-2-dihalogenodeuterioalkanoylamido-1,3-propanediols of formula I.

The D-(threo)-1-p-substitutedphenyl-2-amino-1,3-propanediol precursors are either known compounds or are conveniently prepared according to known procedures. Thus, for example, D-(threo)-1-p-methylsulfonylphenyl-2-amino-1,3-propanediol is conveniently prepared via acid hydrolysis of thiamphenicol (i.e., D-(threo)-1-methylsulfonylphenyl-2-dichloroacetamido-1,3-propanediol).

PHARMACEUTICAL COMPOSITION AND METHOD-OF-USE ASPECTS OF THE INVENTION

The present invention includes within its scope the concept of a pharmaceutical composition comprising a D-(threo)-1-p-substitutedphenyl-2-dihalogenodeuterioalkanoylamido-1,3-propanediol of formula I together with a compatible, pharmaceutically acceptable carrier or coating.

Also included within this invention is the concept of the method of eliciting an antibacterial response in a warm-blooded animal having a susceptible bacterial infection which comprises administering to said animal a non-toxic, antibacterially effective amount of a D-(threo)-1-p-substitutedphenyl-2-dihalogenodeuterioalkanoylamido-1,3-propanediol of formula I.

Also within the scope of this invention is the concept that the deuterio compounds of formula I possess toxicity advantages over their prior art non-deuterated precursors. It has recently been shown [L. P. Pohl, et al., Biochemical Pharmacology 27, 491 (1978)] that the C—H bond of the dichloroacetyl moiety in chloramphenicol is oxidatively cleaved by enzymes in the liver of rats. The resulting hydroxy derivative is unstable and gives a highly reactive acyl chloride which binds to proteins irreversibly. It is my concept that this phenomenon is associated with some of the toxicities of chloramphenicol type antibiotics and that this metabolic process may be slowed down (and thus delay the onset of any resulting toxic effects) by replacing the foregoing C—H bond by a C—D bond in view of the known primary kinetic isotope effect of deuterium in physical and biophysical organic chemistry (see, e.g., N.S. Isaacsin *Experiments in Physical Organic Chemistry*, page 15, The MacMillan Co., London (1969)).

As discussed hereinabove, the D-(threo)-1-p-substituted-phenyl-2-dihalogenodeuterioalkanoyl-1,3-propanediols of formula I are broad spectrum antibacterial agents which, advantageously, exhibit enhanced activity against organisms which are susceptible to their non-deuterated precursors. Thus, the compounds of this invention can be used alone or in combination with other antibiotic agents to prevent the growth or reduce the number of bacteria in various environments. They may be used, for example, to disinfect laboratory glassware, dental and medical equipment contaminated with *Staphylococcus aureus* or other bacteria inhibited by the 3-fluoro-1-propanols of this invention. The activity of the D-(threo)-1-p-substitutedphenyl-2-dihalogenodeuterioalkanoylamido-1,3-propanediols renders them useful for combatting infections caused by gram negative organisms, e.g., species of Proteus and Salmonella or by gram positive organisms, e.g., *Staphylococcus aureus*, and by Ricksettial organisms.

In general, the dosage of D-(threo)-1-p-substitutedphenyl-2-dihalogenodeuterioalkanoylamido-1,3-propanediols will be dependent on the age and weight of animal species being treated, the mode of administration, and the type and severity of bacterial infection being prevented or reduced. In general, the dosage of D-(threo)-1-p-substitutedphenyl-2-dihalogenodeuterioalkanoylamido-1,3-propanediol employed to combat a given infection will be similar to or less than the dosage requirements of the corresponding non-deuterated analog or of chloramphenicol.

The D-(threo)-1-p-substitutedphenyl-2-dihalogenodeuterioalkanoylamido-1,3-propanediols of formula I and the pharmaceutically acceptable salts of esters thereof may be administered parenterally, orally and topically.

The antibacterials of this invention may be utilized in liquid form such as solutions, suspensions, and the like for otic and optic use and may also be administered parenterally via intramuscular injection. The injectable solution or suspension will usually be administered at from about 1 mg. to about 15 mgs. of antibacterial per kilograms of body weight per day divided into about 2 to about 4 doses. The precise dose depends on the stage and severity of the infection, the susceptibility of the infecting organism to the antibacterial and the individual characteristics of the animal species being treated.

For oral administration, the D-(threo)-1-p-substitutedphenyl-2-dihalogenodeuterioalkanoylamido-1,3-propanediol antibacterials may be compounded in the form of tablets, capsules, elixirs or the like or may even be admixed with animal feed. It is in these dosage forms that the antibacterials are most effective for treating bacterial infections of the gastrointestinal tract which infections cause diarrhea.

The D-(threo)-1-p-substitutedphenyl-2-dihalogenodeuterioalkanoylamido-1,3-propanediols may also be applied topically in the form of ointments, both hydrophilic and hydrophobic, in the form of lotions which may be aqueous, non-aqueous or of the emulsion type or in the form of creams. Pharmaceutical carriers useful in the preparation of such formulations will include, for example, such substances as water, oils, greases, polyesters, polyols and the like.

In general, the topical preparations will contain from about 0.1 to about 3 gms. of D-(threo)-1-p-substituted-phenyl-2-dihalogenodeuterioalkanoylamido-1,3-propanediol of formula I per 100 gms. of ointment, cream or lotion. The topical preparations are usually applied gently to lesions from about 2 to 5 times a day.

FORMULATIONS

The following formulations are to exemplify some of the dosage forms in which the antibacterial agents of this invention may be employed. In each, the active ingredient is designated by the term "Drug" which is meant to indicate one of the following compounds:

D-(threo)-1-p-nitrophenyl-2-dichlorodeuterioacetamido-1,3-propanediol; D-(threo)-1-p-methylsulfonylphenyl-2-dichlorodeuterioacetamido-1,3-propanediol; and D-(threo)-1-p-methylsulfonylphenyl-2-difluorodeuterioacetamido-1,3-propanediol. It will be appreciated, however, that each of these compounds may be replaced by equally effective quantities of other compounds defined by formula I.

FORMULATION 1

Oral Suspension

|  | mg/ml |
|---|---|
| Drug, Micronized | 20.0 |
| Sorbitol solution, USP | 250.0 |
| Methylparaben, USP | 0.5 |
| Propylparaben, USP | 0.1 |
| Propylene Glycol, USP | 50.0 |
| Veegum HU (Mg-Aluminum Silicate) | 10.0 |
| Sodium Carboxymethylcellulose | 5.0 |
| Pluronic F-68 | 0.2 |
| Flavor (sufficient) | |
| Purified Water, USP qs ad | 1 ml |

Manufacturing Procedure:

Disperse the Veegum and Sodium carboxymethylcellulose in hot water (80° C.). Add the Sorbitol solution with stirring, followed by the micronized drug. Add the Pluronic F-68 previously dissolved in a portion of hot water (80° C.). Cool the batch to 30° C. Dissolve the Methyl and Propylparaben in the Propylene Glycol. Add the solution to the batch. Add the flavors to the batch. Mix until homogenous.

FORMULATION 2

Ointment

|  | mg/g |
|---|---|
| Drug, Micronized | 20.0 |

-continued

| | mg/g |
|---|---|
| Mineral Oil, USP | 50.0 |
| White Petrolatum, USP qs ad | 1.0 of g. |

Manufacturing Procedure:

Heat the weighed quantity of White Petrolatum and Mineral Oil to 65° and mix until uniform. Cool mixture to 50°–55° C. with stirring. The drug which has been dispersed in a portion of the Mineral Oil and milled, is added to the remainder of the base with stirring. The ointment is cooled to room temperature.

FORMULATION 3

Cream

| | mg/g |
|---|---|
| Drug, Micronized | 20.0 |
| White Petrolatum, USP | 150.0 |
| Mineral Oil, USP | 50.0 |
| Cetomacrogol 1000 | 22.0 |
| Cetyl Alcohol | 40.0 |
| Stearyl Alcohol, USP | 40.0 |
| Sodium Phosphate, Monobasic | 4.0 |
| Propylene Glycol, USP | 50.0 |
| Purified Water qs ad | 1 g |

Manufacturing Procedure:

Dissolve the Propylene Glycol and Monobasic Sodium Phosphate in a specified amount of Purified water at 80°–90° C. A weighed quantity of White Petrolatum, Cetomacrogol 1000, Cetyl Alcohol and Stearyl Alcohol are heated to 70°–75° C., and uniformly mixed. The melted waxes are added to the aqueous portion with stirring while cooling to 45°–50° C. The drug is slurried in a portion of Cetamacrogol dissolved in a specified amount of water. The active slurry is milled, then added to the formula while stirring. The cream is cooled to room temperature.

FORMULATION 4

Lotion

| | mg/g |
|---|---|
| Drug | 20.0 |
| Propylene Glycol, USP | 350.0 |
| Alcohol, USP | 350.0 |
| Hydroxypropylcellulose | 2.5 |
| Purified Water qs ad | 1 g |

Manufacturing Procedure:

Dissolve the drug in Propylene Glycol heated to 50°–60° C. Cool to 30°–35° C. Add the Alcohol and Purified Water with stirring. Disperse the Hydroxypropylcellulose with stirring. Cool to room temperature.

FORMULATION 5

Injectable Solution

| | mg/ml |
|---|---|
| Drug | 250.0 |
| Sodium Tartrate | 1.0 |
| Tartaric Acid | 4.0 |
| N,N-dimethylacetamide | 500.0 |
| Water for Injection qs ad | 1.0 ml |

Manufacturing Procedure:

Dissolve Sodium Tartrate and Tartaric Acid in a portion of Water for Injection. Dissolve the drug in N,N-dimethylacetamide. Mix both solutions and bring it to the final volume with Water for Injection. Aseptically filter the solution through a sterile 0.22 μm teflon (Millipore) membrane.

FORMULATION 6

Sterile Powder

For reconstitution with Water for Injection or normal saline to give final concentration of 100 mg/ml of drug in the solution intended for parenteral use.

Drug (lyophilized) 10    1.0 g

Manufacturing Procedure:

Make a suitable slurry of the drug with Water for Injection and lyophilize it.

FORMULATION 7

Capsules

| Item Ingredient | mg/cap | mg/cap | mg/cap |
|---|---|---|---|
| 1. Drug | 25 | 50 | 250 |
| 2. Lactose Impalpable Powder | 222 | 197 | 185 |
| 3. Corn Starch | 50 | 50 | 60 |
| 4. Magnesium Stearate | 3.0 | 3.0 | 5.0 |
| TOTAL | 300 mg | 300 mg | 500 mg |

Manufacturing Procedure:

Mix Item Nos. 1, 2 and 3 in a suitable mixer. Using a suitable mill, pass the mixture through a No. 40 screen. Add Item No. 4 and mix for 3–5 minutes. Encapsulate the mixture in two-piece hard gelatin capsules, using a suitable capsulating machine.

FORMULATION 8

Tablets

| Item Ingredient | mg/Tab. | mg/Tab. | mg/Tab. |
|---|---|---|---|
| 1. Drug, Micronized | 25 | 50 | 250 |
| 2. Lactose, Impalpable Powder | 202.0 | 177.0 | 234 |
| 3. Microcrystalline Cellulose | 30.0 | 30.0 | 60.0 |
| 4. Corn Starch (10% paste in Water) | 10.0 | 10.0 | 20.0 |
| 5. Corn Starch | 30.0 | 30.0 | 30.0 |
| 6. Magnesium Stearate | 3.0 | 3.0 | 6.0 |
| TOTAL | 300 mg. | 300 mg. | 600 mg. |

Manufacturing Procedure:

Mix Item Nos. 1, 2 and 3 in a suitable blender. Add Item No. 4 and mix until a damp mass is formed. Using a suitable mill, pass the damp mass through a coarse sieve (e.g. No. 6) to yield the granules. Dry the granules for 8–16 hours at 40°–50° C. Mill the dried granules using a suitable mill through a No. 20 sieve. Add Item No. 5 to the milled granules and mix for 5 to 10 minutes. Mix further for 3–5 minutes after the addition of Item No. 6. Compress the mixture into a tablet using a suitable tablet press.

The processes described hereinabove are illustrated in detail hereinbelow in the Preparations and Examples which should not be construed as limiting the scope of my invention, equivalents of the specific disclosure herein will be obvious to those skilled in the art and are contemplated as included within the concept of my invention.

EXAMPLE 1

D-(THREO)-1-p-NITROPHENYL-2-DICHLORODEUTERIOACETAMIDO-1,3-PROPANEDIOL

Add triethylamine (0.7 ml.) to a stirred solution of D-(threo)-1-p-nitrophenyl-2-dichloroacetamido-1,3-propanediol (0.75 gm.) in methyl alcohol-d (i.e., $CH_3OD$) (7 ml.) and stir the solution at room temperature for 18 hours. Concentrate in vacuo and dry the resultant residue in vacuo over phosphorous pentoxide overnight. Dissolve the residue in methanol (5 ml.) and evaporate to dryness. Repeat this procedure once more. Crystallize the resultant residue from an ethyl acetate/N-hexane mixture to obtain D-(threo)-1-p-nitrophenyl-2-dichlorodeuterioacetamido-1,3-propanediol; Mass spectrum: M+ 324: pmr (dmso-d$_6$): δ8.38 (d, J=10.0 Hz, NH); 7.82 (ABq, J=8.0 Hz, aromatic hydrogens); 5.95 (d, J=4.0 Hz, benzylic-OH), 4.9 (t, J=5.0 Hz, 3-OH).

EXAMPLE 2

D-(THREO)-1-p-METHYLSULFONYLPHENYL-2-DICHLORODEUTERIOACETAMIDO-1,3-PROPANEDIOL

In a manner similar to that described in Example 1, treat D-(threo)-1-p-methylsulfonylphenyl-2-dichloroacetamido-1,3-propanediol with methyl alcohol-d in the presence of triethylamine and isolate and purify the resultant product in a manner similar to that described to obtain D-(threo)-1-p-methylsulfonylphenyl-2-dichlorodeuterioacetamido-1,3-propanediol; Mass spectrum: M+ 357: pmr (dmso-d$_6$): δ8.37 (d, J=9.0 Hz, NH); 7.83 (ABq, J=8.0 Hz, aromatic hydrogens); 5.88 (d, J=4.0 Hz, benzylic-OH); 4.87 (t, J=6.0 Hz, 3-OH).

EXAMPLE 3

D-(THREO)-1-p-METHYLSULFONYLPHENYL-2-DIFLUORODEUTERIOACETAMIDO-1,3-PROPANEDIOL

In a manner similar to that described in Example 1, treat D-(threo)-1-p-methylsulfonylphenyl-2-difluoroacetamido-1,3-propanediol with methanol-d in the presence of triethylamine and isolate and purify the resultant product in a manner similar to that described to obtain D-(threo)-1-methylsulfonylphenyl-2-difluorodeuterioacetamido-1,3-propanediol.

Similarly, by treating D-(threo)-1-p-nitrophenyl-2-difluorodeuterioacetamido-1,3-propanediol with methanol-d in a manner similar to that described in Example 1, there is obtained D-(threo)-1-p-nitrophenyl-2-difluorodeuterioacetamido-1,3-propanediol.

EXAMPLE 4

D-(THREO)-1-p-NITROPHENYL-2-(R,S-CHLOROFLUORODEUTERIOACETAMIDO)-1,3-PROPANEDIOL

A. D-(THREO)-1-p-Nitrophenyl-2-(R,S-Chlorofluoroacetamido)-1,3-Propanediol

Add triethylamine (0.2 ml.) to a solution of D-(threo)-1-p-nitrophenyl-2-amino-1,3-propanediol (1.1 gm.) and ethyl chlorofluoroacetate (0.5 ml.) in ethanol (14 ml.). Heat at reflux temperature under a blanket of nitrogen for two hours. Add an additional amount of ethyl chlorofluoroacetate (0.5 ml.) and continue heating until the reaction is essentially complete as indicated by the absence of starting compound as determined by thin layer chromatography using a mixture of chloroform and ethanol (97:3) as the solvent system. Evaporate the solvents in vacuo and chromatograph the resultant residue on silica gel (40 gm.) using chloroform as the eluant. Collect like fractions containing the desired product as determined by thin layer chromatography, evaporate to dryness in vacuo to obtain D-(threo)-1-p-nitrophenyl-2-(R,S-chlorofluoroacetamido)-1,3-propanediol; Mass spectrum: (M+ +1) 307; pmr: (dmso-d$_6$): δ8.28 (d, J=10 Hz, NH); 7.83 (ABq, J=10 Hz, aromatic hydrogens); 6.80 (q, J=50 Hz and 2 Hz, CHClF); 5.90 (d, J=4 Hz, benzylic-OH); 5.0 (m, H-1); 4.87 (t, J=5.0 Hz, 3-OH).

B. D-(Threo)-1-p-Nitrophenyl-2-(R,S-Chlorofluorodeuterioacetamido)-1,3-Propanediol In a manner similar to that described in Example 1, treat D-(threo)-1-p-nitrophenyl-2-(R,S-chlorofluoroacetamido)-1,3-propanediol with methyl alcohol-d in the presence of triethylamine and isolate and purify the resultant product in a manner similar to that described to obtain D-(threo)-1-p-nitrophenyl-2-(R,S-chlorofluorodeuterioacetamido)-1,3-propanediol.

EXAMPLE 5

D-(THREO)-1-p-METHYLSULFONYLPHENYL-2-(R,S-CHLOROFLUORODEUTERIOACETAMIDO)-1,3-PROPANEDIOL

A. D-(Threo)-1-p-Methylsulfonylphenyl-2-Amino-1,3-Propanediol Hydrochloride

Suspend D-(threo)-1-p-methylsulfonylphenyl-2-dichloroacetamido-1,3-propanediol (71 gm., 200 mmol) in water (300 ml.) containing concentrated hydrochloric acid (25 ml.). Stir the reaction mixture at reflux temperature for six hours, then evaporate to dryness in vacuo. Add toluene (100 ml.) to the resultant residue and evaporate. Repeat this procedure again and dry the residue comprising D-(threo)-1-p-methylsulfonylphenyl-2-amino-1,3-propanediol hydrochloride.

B. D-(Threo)-1-p-Methylsulfonylphenyl-2-(R,S-Chlorofluoroacetamido)-1,3-Propanediol Dissolve the compound obtained in Example 5A in ethanol (200 ml.), then add one equivalent of 1 N sodium hydroxide with stirring followed by triethylamine (14 ml.) and ethylchlorofluoroacetate (35 ml.). Heat at reflux temperature under a blanket of nitrogen for 2 hours, add an additional amount of ethylchlorofluoroacetate (35 ml.) and continue heating until the reaction is essentially complete as determined by thin layer chromatography using a mixture of chloroform:ethyl (97:3) as the solvent system. Evaporate the reaction mixture in vacuo and and chromatograph the resultant residue on silica gel using chloroform as the eluant. Collect the like homogeneous fractions as determined by thin layer chromatography and evaporate to dryness in vacuo to obtain D-(threo)-1-p-methylsulfonylphenyl-2-(R,S- chlorofluoroacetamido)-1,3-propanediol; Mass spectrum: (M++1) 340, other characteristic fragments at m/e 186, 185, 171, 156, 154, 139, 138, 137, 136, 123, 121, 118, 117, 108, 107, 106, 105, 102, 95, 91, 90, 89, 81, 79, 78, 77, 76, 70, 69, 67, 65, 63, 60, 52, 51 and 50.

C.
D-(Threo)-1-p-Methylsulfonylphenyl-2-(R,S-Chlorofluorodeuterioacetamido)-1,3-Propanediol Treat D-(threo)-1-p-methylsulfonylphenyl-2-(R,S-chlorofluoroacetamido)-1,3-propanediol with methanol-d and triethylamine in a manner similar to that described in Example 1, then isolate and purify the resultant product in a similar manner to obtain D-(threo)-1-p-methylsulfonylphenyl-2-(R,S-chlorofluorodeuterioacetamido)-1,3-propanediol.

EXAMPLE 6
OTHER D-(THREO)-1-p-NITROPHENYL (OR 1-p-METHYLSULFONYLPHENYL)-2-DIHALOGENODEUTERIOACETAMIDO (OR $\alpha,\beta$-DIHALOGENO-$\alpha$-DEUTERIOPROPIONAMIDO)-1,3-PROPANEDIOLS

A. D-(Threo)-1-p-Nitrophenyl (or 1-p-Methylsulfonylphenyl)-2-Dibromodeuterioacetamido-1,3-propanediol (1) In a manner similar to that described in Examples 4A and 5B, treat each of D-(threo)-1-p-nitrophenyl-2-amino-1,3-propanediol and D-(threo)-1-p-methylsulfonylmethyl-2-amino-1,3-propanediol in methanol or ethanol with methyl dibromoacetate. Isolate and purify each of the resulting products in a manner similar to that described to obtain, respectively, D-(threo)-1-p-nitrophenyl-2-dibromoacetamido-1,3-propanediol and D-(threo)-1-p-methylsulfonylphenyl-2-dibromoacetamido-1,3-propanediol.

(2) Treat each of the products of Example 6A(1) with methyl alcohol-d in a manner similar to that described in Example 1 to obtain, respectively, D-(threo)-1-p-nitrophenyl-2-dibromodeuterioacetamido-1,3-propanediol and D-(threo)-1-p-methylsulfonylphenyl-2-dibromodeuterioacetamido-1,3-propanediol.

B. D-(Threo)-1-p-Nitrophenyl (or 1-p-Methylsulfonylphenyl)-2-($\alpha,\beta$-Dihalogeno-$\alpha$-deuteriopropionamido)-1,3-Propanediol (1) To D-(threo)-1-p-nitrophenyl-2-amino-1,3-propanediol (0.428 g., 2 mmol.), add ethanol (5 ml.) and triethylamine (0.202 g., 2 mmol.). Cool the solution to 5° C. with stirring and then add, dropwise, $\alpha,\beta$-dichloropropionyl chloride (0.322 g., 2 mmol.). After 30 minutes at room temperature, isolate and purify the resultant product in a manner similar to that described in method 4A to obtain D-(threo)-1-p-nitrophenyl-2-($\alpha,\beta$-dichloropropionamido)-1,3-propanediol.

(2) In the procedure of Example 6B(1), by substituting an equivalent quantity of $\alpha,\beta$-difluoroacetyl chloride for $\alpha,\beta$-dichloropropionyl chloride, there is obtained D-(threo)-1-p-nitrophenyl-2-($\alpha,\beta$-difluoropropionamido)-1,3-propanediol.

(3) Treat D-(threo)-1-p-methylsulfonylphenyl-2-amino-1,3-propanediol with each of $\alpha,\beta$-dichloropropionylchloride and $\alpha,\beta$-difluoropropionyl chloride in a manner similar to that described in Examples 6B(1 and 2) to obtain, respectively, D-(threo)-1-p-methylsulfonylphenyl-2-($\alpha,\beta$-dichloropionamido)-1,3-propanediol and D-(threo)-1-p-methylsulfonylphenyl-2-($\alpha,\beta$-difluoropropionamido)-1,3-propanediol.

(4) Treat each of the products of Examples 6B(1-4) with methyl alcohol-d and triethylamine in the manner of Example 1 to obtain, respectively, D-(threo)-1-p-nitrophenyl-2-($\alpha,\beta$-dichloro-$\alpha$-deuteriopropionamido)-1,3-propanediol, D-(threo)-1-p-nitrophenyl-2-($\alpha,\beta$-difluoro-$\alpha$-deuteriopropionamido)-1,3-propanediol, D-(threo)-1-p-methylsulfonylphenyl-2-($\alpha,\beta$-dichloro-$\alpha$-deuteriopropionamido)-1,3-propanediol, and D-(threo)-1-p-methylsulfonylphenyl)-2-($\alpha,\beta$-difluoro-$\alpha$-deuteriopropionamido)-1,3-propanediol.

EXAMPLE 7
D-(THREO)-1-p-SUBSTITUTEDPHENYL-2-DICHLORODEUTERIOACETAMIDO-1,3-PROPANEDIOLS

In a manner similar to that described in Example 1, treat each of the following 1,3-propanediols with methyl alcohol-d and triethylamine: D-(threo)-1-p-methylthiophenyl-2-dichloroacetamido-1,3-propanediol and D-(threo)-1-p-sulfinylphenyl-2-dichloroacetamido-1,3-propanediol. Isolate and purify each of the resultant products in a manner similar to that described to obtain, respectively, D-(threo)-1-p-methylthiophenyl-2-dichlorodeuterioacetamido-1,3-propanediol and D-(threo)-1-p-methylsulfinyl-2-dichlorodeuterioacetamido-1,3-propanediol.

EXAMPLE 8
SODIUM D-(THREO)-1-p-NITROPHENYL-2-DICHLORODEUTERIOACETAMIDO-1,3-PROPANEDIOL HEMI-SUCCINATE

To D-(threo)-1-p-nitrophenyl-2-dichlorodeuterioacetamido-1,3-propanediol (1.3 gm., 4 mmols) in dioxane (12 ml.) add succinic anhydride (0.46 gm., 4 mmols) and triethylamine (2.4 ml.). Allow the solution to stand at room temperature for 6 hours, then evaporate to a small volume and dissolve the resultant residue in chloroform (200 ml.). Wash the chloroform solution with dilute hydrochloric acid then wash with water; dry over magnesium sulfate, filter and evaporate. Recrystallize the resultant residue from diethylether to obtain D-(threo)-1-p-nitrophenyl-2-dichlorodeuterioacetamido-1,3-propanediol succinate.

Dissolve D-(threo)-1-p-nitrophenyl-2-dichlorodeuterioacetamido-1,3-propanediol succinate (850 mg., 2 mmols) in water, add sodium bicarbonate (168 mg., 2 mmols), stir for 15 minutes, filter, add water to the filtrate, then evaporate to a residue comprising sodium D-(threo)-1-p-nitrophenyl-2-dichlorodeuterioacetamido-1,3-propanediol hemi-succinate.

I claim:

1. A D-(threo)-1-aryl-2-acylamido-1,3-propanediol of the following formula:

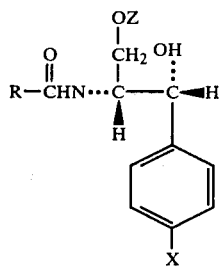

wherein R is a member selected from the group consisting of dihalogenodeuteriomethyl and 1,2-dihalogeno-1-deuterioethyl;

X is a member selected from the group consisting of $NO_2$, $SO_2R_1$, $SOR_1$, $SR_1$, $SONH_2$, $SO_2NH_2$, $SONHR_1$, $SO_2NHR_1$, $COR_1$, CN, halogen, hydrogen, phenyl, and phenyl substituted by halogen, $NO_2$ or $SO_2CH_3$, wherein $R_1$ is a member selected from the group consisting of methyl, ethyl, n-propyl and isopropyl; and Z is a member selected from the group consisting of hydrogen, an acyl radical of a hydrocarboncarboxylic acid having up to 16 carbon atoms, an acyl radical of a hydrocarbondicarboxylic acid having up to 16 carbon atoms, and an acyl radical of an aminohydrocarboncarboxylic acid having up to 12 carbon atoms; and the pharmaceutically acceptable salts of said acyl radicals.

2. A compound of claim 1 wherein Z is hydrogen.

3. A compound of claims 1 or 2 wherein X is $NO_2$, $SO_2R_1$, or $SO_2NH_2$.

4. A compound of claim 3 wherein R is dichlorodeuteriomethyl or difluorodeuteriomethyl or chlorofluorodeuteriomethyl.

5. A compound of claim 4 wherein R is dichlorodeuteriomethyl, X is nitro and Z is hydrogen, said compound being D-(threo)-1-p-nitrophenyl-2-dichlorodeuterioacetamido-1,3-propanediol.

6. A compound of claim 4 wherein R is dichlorodeuteriomethyl, X is methylsulfonyl, and Z is hydrogen, said compound being D-(threo)-1-p-methylsulfonylphenyl-2-dichlorodeuterioacetamido-1,3-propanediol.

7. A compound of claim 4 wherein R is chlorofluorodeuteriomethyl, X is nitro, and Z is hydrogen, said compound being D-(threo)-1-p-nitrophenyl-2-chlorofluorodeuterioacetamido-1,3-propanediol.

8. A compound of claim 4 wherein R is chlorofluorodeuteriomethyl, X is methylsulfonyl, and Z is hydrogen, said compound being D-(threo)-1-p-methylsulfonylphenyl-2-chlorofluorodeuterioacetamido-1,3-propanediol.

9. A compound according to claim 4 wherein R is difluorodeuteriomethyl, X is methylsulfonyl, and Z is hydrogen, said compound being D-(threo)-1-p-methylsulfonylphenyl-2-difluorodeuterioacetamido-1,3-propanediol.

10. A compound according to claim 4 wherein Z is an acyl radical of an acid selected from the group consisting of succinic acid, palmitic acid, pantothenic acid, and aminoacetic acid.

* * * * *